US012048352B2

(12) United States Patent
Haimerl

(10) Patent No.: US 12,048,352 B2
(45) Date of Patent: Jul. 30, 2024

(54) SHOE HAVING A FOOT-STIMULATING DEVICE

(71) Applicant: HERO GMBH & CO. KG, Mainburg (DE)

(72) Inventor: Ewald Haimerl, Mainburg (DE)

(73) Assignee: HERO GMBH & CO. KG, Mainburg (DE)

(*) Notice: Subject to any disclaimer, the term of this patent is extended or adjusted under 35 U.S.C. 154(b) by 496 days.

(21) Appl. No.: 16/015,728

(22) Filed: Jun. 22, 2018

(65) Prior Publication Data
US 2018/0368511 A1 Dec. 27, 2018

(30) Foreign Application Priority Data
Jun. 22, 2017 (DE) ...................... 10 2017 113 846.3

(51) Int. Cl.
| A43B 7/1455 | (2022.01) |
| A41B 11/00 | (2006.01) |
| A43B 3/00 | (2022.01) |
| A43B 7/14 | (2022.01) |
| A43B 7/142 | (2022.01) |
| A43B 7/1435 | (2022.01) |
| A43B 7/1445 | (2022.01) |
| A43B 13/14 | (2006.01) |
| A43B 23/00 | (2006.01) |
| A61F 13/06 | (2006.01) |
| A43C 1/00 | (2006.01) |

(52) U.S. Cl.
CPC .......... *A43B 7/1455* (2013.01); *A41B 11/003* (2013.01); *A43B 3/0036* (2013.01); *A43B 7/142* (2013.01); *A43B 7/1435* (2013.01); *A43B 7/1445* (2013.01); *A43B 7/1495* (2013.01); *A43B 13/14* (2013.01); *A43B 23/00* (2013.01); *A61F 13/067* (2013.01); *A41B 2400/32* (2013.01); *A43C 1/00* (2013.01)

(58) Field of Classification Search
CPC ......... A43C 1/00; A43B 5/0447; A43B 7/142; A43B 7/1435; A43B 7/1445; A43B 7/1455; A43B 7/1495; A43B 13/14; A43B 23/00; A43B 3/0036; A43B 2400/32; A41H 1/02; A61F 13/067
USPC .................................................. 36/170; 2/239
See application file for complete search history.

(56) References Cited

U.S. PATENT DOCUMENTS

| 2,259,273 A * | 10/1941 | Smith ..................... A43B 3/122 D2/918 |
| 2,389,148 A * | 11/1945 | Grebow ................ A43B 7/1495 36/76 R |
| 2,933,834 A * | 4/1960 | Bourland ............. A43B 7/1495 36/170 |

(Continued)

OTHER PUBLICATIONS

Examination Report from German Patent Office for Application No. 10 2017 113 846.3, Feb. 22, 2018, pp. 1-7.

*Primary Examiner* — Jocelyn Bravo
(74) *Attorney, Agent, or Firm* — SALIWANCHIK, LLOYD & EISENSCHENK

(57) ABSTRACT

Shoe which has a band-like device which extends from the upper shaft end to the shoe base on one inner side of the shoe and extends from the shoe base in the direction of the upper shaft end on the opposite inner side of the shoe, wherein the band-like device is designed to exert pressure on a foot arranged in the shoe.

11 Claims, 3 Drawing Sheets

(56) References Cited

U.S. PATENT DOCUMENTS

| | | | | |
|---|---|---|---|---|
| 3,323,232 A * | 6/1967 | Danowsky | A43B 7/1495 | 36/76 R |
| 3,327,410 A | 6/1967 | Park, Sr. et al. | | |
| 4,411,077 A * | 10/1983 | Slavitt | A43B 5/00 | 36/114 |
| 4,476,639 A * | 10/1984 | Zaccaria | A43C 11/1493 | 36/114 |
| 4,550,511 A * | 11/1985 | Gamm | A43B 7/1495 | 36/91 |
| 4,592,154 A * | 6/1986 | Oatman | A43C 1/003 | 36/114 |
| 4,753,229 A * | 6/1988 | Sutherland | A61F 13/066 | 602/27 |
| 4,860,464 A * | 8/1989 | Misevich | A43B 7/1495 | 36/114 |
| 4,982,733 A * | 1/1991 | Broadhurst | A61F 5/0111 | 602/27 |
| 5,109,613 A * | 5/1992 | Van Dyke | A43B 7/20 | 36/114 |
| 5,269,078 A * | 12/1993 | Cochrane | A43B 7/20 | 36/93 |
| 5,323,549 A * | 6/1994 | Segel | A43B 7/1495 | 36/170 |
| 5,771,608 A * | 6/1998 | Peterson | A43B 5/00 | 36/50.1 |
| 5,819,439 A * | 10/1998 | Sanchez | A43B 5/00 | 36/89 |
| 5,992,057 A * | 11/1999 | Monti | A43B 5/02 | 36/50.1 |
| 6,393,733 B1 * | 5/2002 | London | A43B 7/1495 | 36/170 |
| 6,505,424 B2 * | 1/2003 | Oorei | A43B 5/00 | 36/129 |
| 6,772,541 B1 * | 8/2004 | Ritter | A43B 7/14 | 36/50.1 |
| 6,925,734 B1 * | 8/2005 | Schaeffer | A43B 7/1495 | 36/169 |
| 2007/0283597 A1 * | 12/2007 | Logan | A61F 5/0111 | 36/91 |
| 2014/0013618 A1 | 1/2014 | Ruthven et al. | | |
| 2016/0166419 A1 | 6/2016 | Jones et al. | | |
| 2016/0309844 A1 * | 10/2016 | Smith | A43C 11/1493 | |
| 2017/0071285 A1 | 3/2017 | Syed et al. | | |

* cited by examiner

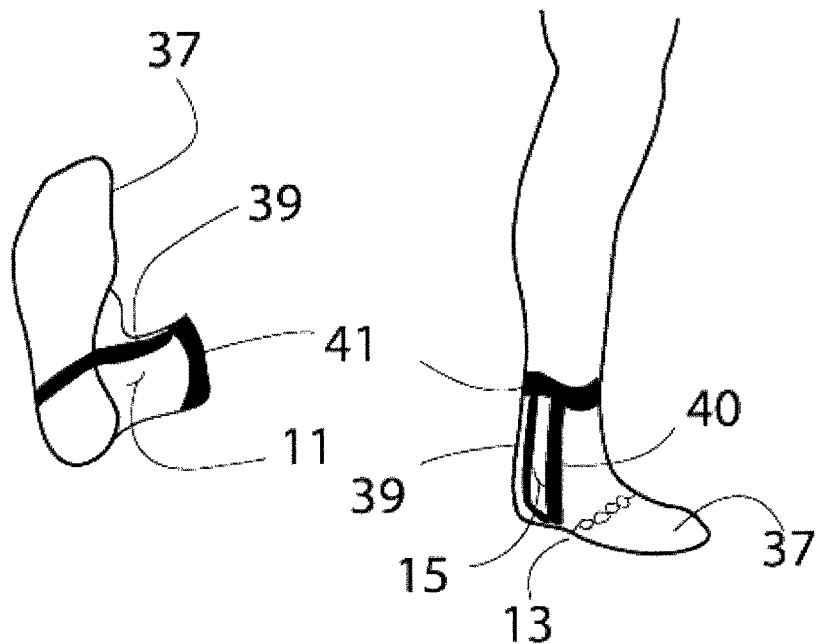
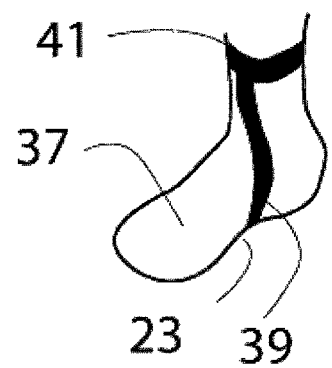
FIG. 4A    FIG. 4B    FIG. 4C
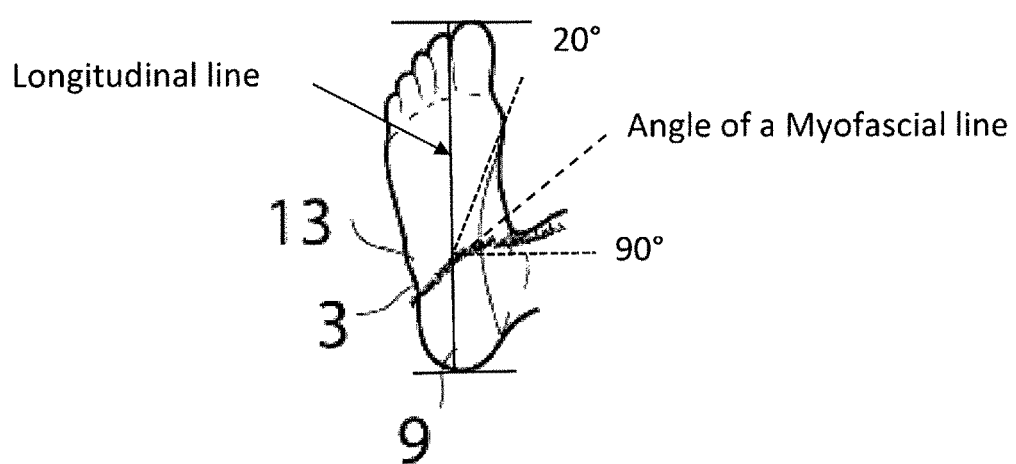
FIG. 5

SHOE HAVING A FOOT-STIMULATING DEVICE

CROSS REFERENCE TO A RELATED APPLICATION

This application claims priority under 35 U.S.C. § 119(e) of German Patent Application No. DE 10 2017 113 846.3, filed Jun. 22, 2017, which is incorporated herein by reference in its entirety.

FIELD OF THE INVENTION

The invention relates to a shoe having a foot-stimulating device, to a sole and to a sock. Ideally, the foot and the shoe of the wearer form a functional unit which is formed by the basic fit of the shoe and by an additional fastening possibility, for example lacing or one or more buckles. The shoe is intended to protect the foot from external influences, for example cold, moisture, injuries, and also to impede physiological functions, such as the gait, including the natural rolling motion, as little as possible.

BACKGROUND OF THE INVENTION

Even in a largely optimized shoe, it is not possible to prevent the shoe from influencing, and possibly at least slightly restricting, the natural function and natural surroundings of the foot on account of the construction, the selected materials and the function of said shoe.

It is the object of the invention to compensate for or reduce these restrictions of the foot, which can lead to non-physiological stress and to fatigue, by stimulating particular regions of the foot.

BRIEF SUMMARY OF THE INVENTION

The object is achieved by a shoe which has a band-like device which extends from a point at the upper shaft end or in the vicinity of the upper shaft end to the shoe base on one inner side of the shoe and extends from the shoe base in the direction of the upper shaft end on the opposite inner side of the shoe, wherein the band-like device is designed to exert contact by pressure on a foot arranged in the shoe. The band-like device can have one, two or more band-like sections. A one-part band-like device can extend from a point at the upper shaft end or in the vicinity of the upper shaft end to the shoe base on one inner side of the shoe, cross the shoe base and extend in the direction of the upper shaft end on the opposite inner side of the shoe. One or both ends or sections of the band-like device can extend as far as the upper shaft end. At least one end of the band-like device or of a section thereof can also end at the shoe base, however, and be secured to the shoe or to the inner sole there. The band-like device can cross the shoe base at an angle of between 20° and 90° (i.e. for example at 20°, 30°, 40°, 50°, 60°, 70°, 80° or 90° to the longitudinal direction of the shoe. When both ends of the band-like device or of the sections extend from the shoe base in the direction of the shaft edge on the opposite inner sides of the shoe, then, according to one embodiment, that section of the band-like device that extends on the big-toe side of the shoe extends in front of the position of the medial malleolus of a foot arranged in the shoe, while that section of the band-like device that extends on the little-toe side of the shoe extends upwards behind the position of the lateral malleolus of the foot arranged in the shoe.

According to one embodiment, both sections of the band-like device extend, at least in the upper part of the shoe, substantially vertically upwards in the direction of the shaft edge. However, it is also conceivable for one or both sections to extend upwards at an angle of between 0° and 45° with respect to the perpendicular to the sole of the shoe or to extend in this direction. The angle can be in particular between 20° and 70°, between 30° and 60° or between 35° and 55° (degrees) and be different for each section. The sections extend preferably in a rectilinear manner in the stated directions, but could also have a curved or arcuate course.

By way of the band-like device, according to the present invention, provided in the shoe, it is possible for regions of the foot that are located in the region of the band-like device to be stimulated by exertion of pressure and in this way for functions of the foot and of the lower leg, which are impaired or disrupted in a conventional shoe, to be activated throughout the period in which a shoe is worn. Depending on the configuration of the band-like device, in particular the thickness or size thereof, the exerted pressure can be scarcely perceptible or clearly noticeable to the wearer of the shoe. It is also possible for the pressure exerted by the band-like device to vary in intensity in one or more regions of the band-like device. If the band-like device extends for example in the shoe over the region of the Achilles tendon, the band-like device can be designed in a thinner manner or be hollowed at this point, in order to avoid rubbing on the foot. These regions can have for example a length of 1 cm to 5 cm, in particular 1 cm, 2 cm, 3 cm, 4 cm, 5 cm or more.

According to one preferred embodiment, the band-like device is arranged in the shoe such that it exerts pressure on myofascial lines of the foot. In particular, the band-like device can be arranged in the shoe such that it extends at least partially along one or more myofascial lines of the foot.

The human body has a large number of myofascial lines, with which the musculoskeletal system of the human body is moved and tensed in a controlled manner. The myofascial lines allow humans to stand upright, to adapt to different situations, to work in different positions and to carry out tasks. The most important myofascial lines, which cover the body, are located close together in the foot and can start there. Significant myofascial lines are the superficial back line 1, the superficial front line 5, the lateral lines 7, the deep front line and the spiral line 3, which extend over the entire body and also continue in the foot 9, as is shown in FIG. 1. Particularly noteworthy is the myofascial spiral line 3, which extends on the foot in the region of the talocalcaneonavicular joint and the tarsus and encloses and bunches the other myofascial lines 1, 5 and 7.

The myofascial spiral line 3 extends like a double helix around the human body. It connects the sides of the skull in each case to the opposite shoulder via the upper back, then extends around the ribs, crosses the other spiral line of the double helix on the front side of the abdomen and extends down the thighs and lower legs to the inner side of the longitudinal arch of the foot, then through under the foot 9 to the outside of the foot 9 and upwards behind the lateral malleolus to the outside of the lower leg and to the ischium and from there back over the back to the skull (cf. Thomas B. Meiers, Anatomy Trains—Myofasziale Leitbahnen [Myofascial pathways], Urban and Fischer, 2nd edition, 2010).

At the tarsus, the myofascial spiral line 3 crosses a region which is activated upon any loading of the foot and thus absorbs the entire weight of the body and distributes it to the forefoot and rearfoot.

Accordingly, in one embodiment, the band-like device according to the invention is arranged in the shoe such that it at least partially follows the myofascial spiral line 3 of a foot positioned in the shoe and activates or stimulates the muscles and tendons thereof. Preferably, the myofascial spiral line 3 is activated by targeted contact, which results in areal stimulation.

According to a further embodiment, the band-like device is arranged in the shoe such that it crosses the shoe bottom at the arch of the foot, in particular in the region of the talocalcaneonavicular joint. At this position, the band-like device is located opposite the myofascial spiral line on the underside of the foot.

Depending on the shaft height of the shoe, the band-like device at least partially follows the course of the myofascial spiral line on the foot from the front edge of the lower leg outside the front edge of the shin in the direction of extension of the front shin muscle to the inside of the tarsus, from where the myofascial spiral line winds around the head of the anklebone (talus) and of the navicular bone and extends obliquely over the sole of the foot on the outside of the foot in the heelward direction of the base of the fifth metatarsal and then rises behind the lateral malleolus to the fibula and runs out at the head of the fibula. According to a further embodiment, the band-like device is arranged in the shoe such that it crosses the shoe bottom starting from the location of the base of the fifth metatarsal of the foot arranged in the shoe.

According to a further embodiment, the band-like device is arranged at least partially under the inner lining of the shoe. The band-like device can be fastened for example to the material, in particular upper, of the shoe on the inner side thereof, in particular sewn thereto, adhesively bonded thereto or integrated therein. For example, it is possible to provide in the material of the shoe a cutout, pocket, loop, in which the band-like device is at least partially or entirely arranged. The band-like device can also be integrated into the inner lining of the shoe, however. The band-like device can also be integrated into the lacing such that, as a result of the lacing being tied, pressure is exerted on the foot in the region of the spiral line by the band-like device, which serves to activate the foot. For example, at least one end of the band-like device can have one or more eyelets or hooks, through which a lace can be passed. At least one end of the band-like device could also be fastened to a strip or an edging of the entry opening of the shoe, eyelets or hooks of the lacing or a hook-and-loop fastener being arranged in said strip or edging.

According to a further embodiment, the band-like device is configured as part of the inner lining of the shoe. The band-like device could for example be integrated into the inner lining, in particular sewn in or woven in.

According to a further embodiment, the band-like device is configured as a cushion or as a flat band made of a fabric or textile, for example as a cord. In the case of a cushion, the pressure on the foot in the region of at least one of the myofascial lines of the foot that extend in this region, in particular of the myofascial spiral line, can be brought about solely by the weight force of the wearer of the shoe, without it being necessary to tension the band-like device. In the case of a band-like device formed with a cord, for pressure exertion, tensioning with the aid of a hook-and-loop fastener or some other closing or fixing device may be necessary.

According to one embodiment, the band-like device has a width of between 1 and 5 cm, in particular a width of 1 cm, 2 cm, 3 cm, 4 cm or 5 cm.

According to another embodiment, the band-like device is formed at least sectionally from an elastic material, i.e. it has at least one section made of an elastic material. This section can have a length of between 1 and 5 cm, in particular a length of 1 cm, 2 cm, 3 cm, 4 cm or 5 cm. In this embodiment, as a result of a pull exerted on the band-like device, said pull being brought about by at least one of the ends being secured, for example by a fastener, to the shoe, pressure can be exerted on one or more myofascial lines in the foot of the wearer. It is conceivable to produce sections of the band-like device or the entire band-like device from an elastic material.

According to a further embodiment, the shoe has, at least on the outer side of the shaft, at least one opening, through which one end of the band-like device can be passed from the inside of the shoe to the outside.

On the outer side of the shoe, the band-like device can be tensioned with the other end of the band-like device, optionally in conjunction with lacing of the shoe, by means of an eyelet or a button or hook on the shoe, such that pressure can be exerted on one or more myofascial lines of the foot of the wearer.

According to a further embodiment, the inner sole of the shoe has, on its top side or underside, a recess crossing the inner sole, the band-like device being arranged in said recess. The recess serves to guide the band-like device in the region of the sole. According to one embodiment, the recess extends from the inside of the shoe, in the region of the arch of the foot, to the outside of the shoe in the region of the lateral malleolus. Alternatively, the recess can also extend from the region of the arch of the foot to the base of the fifth metatarsal. Rather than a recess, a closed channel could also be provided, which is formed in the sole.

According to one embodiment, the band-like device together with the recess extends at an angle of between 20° and 90°, in particular 30° and 80°, 40° and 70°, 50° and 60° (degrees) to the longitudinal direction of the sole.

According to yet another embodiment, the band-like device is arranged under the inner sole of the shoe.

According to a further embodiment, at least one channel or one or more eyelets or loops are formed in the inner lining or on the inner side of the shoe under the inner lining, the band-like device being able to be received therein. The channel or the eyelet(s) or loop(s) have the function of keeping the band-like device on the inner side of the shoe in the region of the corresponding myofascial line(s) extending there.

According to a further embodiment, the band-like device has two ends, at least one of which branches into two ends. It is also possible for the ends on both sides of the sole to branch in each case into two or even more ends. The branching of the at least one end occurs in accordance with the course of the myofascial line on the inside or outside of the foot and the branching thereof. In particular, one of the ends of the branching band-like device can extend on the inner side of the shoe from the shoe base in the direction of the position of the medial malleolus and behind the medial malleolus of the foot to the Achilles tendon. A further end of the branching band-like device on the opposite inner side of the shoe can extend from the shoe base in the direction of the lateral malleolus and then behind the lateral malleolus in the direction of the head of the fibula. The respective other ends preferably follow the above-described course of the other lines of the myofascial spiral line.

According to a further embodiment, the band-like device has a fastener, with which the two ends, or in the case of branching optionally additional ends, of the band-like device can be joined together. In this way, the band-like device in the interior of the shoe or on the outer side can be closed over the foot and pressure can be exerted on the myofascial lines of the foot in accordance with the arrangement of the band-like device facing the at least one myofascial line.

According to a further embodiment, the band-like device has, at least at one end, one or more components of a hook-and-loop fastener, such that one end of the band-like device, which has a component of the hook-and-loop fastener, can be folded back onto another section of the same end of the band-like device having the other component of the hook-and-loop fastener once the end has been passed through one or more eyelets on the shoe.

Other types of fastener are also conceivable, however, in order to fix one or both ends of the band-like device to the shoe or to join them together, for example a clamping fastener or a buckle.

According to yet another embodiment, the band-like device has, on the inside, a channel for holding a fluid which can be pressurized. The fluid can be for example a gas, a liquid or a memory material.

According to a further embodiment, the shoe can additionally have at least one further band-like device, which is separate from the other band-like device or forms a part thereof. According to yet another embodiment, the further band-like device can be configured as a cushion which is integrated into the inner lining of the shoe, while the other band-like device is formed for example by a cord or a textile fabric. Such a combination of materials is conceivable even in the case of a band-like device having one or two branched ends, wherein the branched ends are formed from different materials, in particular as a cushion and as a cord or a textile fabric.

The further band-like device can be arranged in the shoe in a manner corresponding to the location of further myofascial lines which extend on the front side of the lateral malleolus and/or on the inside of the heel in the region of the Achilles tendon. As a result, additional holding functions, primarily of a passive but also of an active type, can be achieved by acting on for example the myofascial chain of the deep front line. Preferably, the band-like device which corresponds to the course of the myofascial spiral line should always be present. According to one embodiment, at least one end of the band-like device is joined to the lacing.

If the band-like device is integrated into the lacing, slight pressure is exerted on the skin in the region of the myofascial spiral line as a result of the lacing being tied, said pressure stimulating the activation of said myofascial spiral line.

According to a further embodiment, at least one end of the band-like device is secured to the shoe, in particular on the inner side. This embodiment provides for a pull to be exerted only on an end of the band-like device that is not secured in order to secure this end to the shoe, in particular on the outer side of the shoe or in conjunction with the lacing, in order to tension the band-like device and to exert pressure on the myofascial lines in the foot of the wearer.

According to the invention, a shoe sole, in particular a shoe inner sole, is furthermore provided, which has a band-like device which is connected to the sole and extends at an angle to the longitudinal direction of the sole.

By way of the band-like device integrated into or joined to the shoe sole, sections of the foot that are located in the region of the band-like device can be stimulated by exertion of pressure and thus the functions of the foot and of the lower leg that are impaired or disrupted in a conventional shoe can be activated for the duration that the sole according to the invention is worn. The exerted pressure can be scarcely perceptible or clearly noticeable to the wearer of the shoe depending on the configuration of the band-like device. It is also possible for the pressure exerted by the band-like device to vary in intensity in different regions of the band-like device.

According to one preferred embodiment, the band-like device is arranged on or integrated into the sole that exerts pressure on the myofascial lines of the foot. In particular, the band-like device can be arranged on the sole such that it extends at least partially along one or more myofascial lines of the foot.

With such an inner sole, which can be inserted into a shoe or boot, particular myofascial lines in the foot which come into contact with the band-like device can be stimulated. In particular, with the shoe sole, pressure is exerted on one or more myofascial lines in the foot. The pressure can be created for example by the body weight when a shoe having the shoe sole according to the invention is worn.

According to a further embodiment, the band-like device is arranged on or integrated into the sole such that it crosses the shoe bottom at the arch of the foot, in particular in the region of the talocalcaneonavicular joint. At this position, the band-like device is located opposite the myofascial spiral line on the underside of the foot.

According to one embodiment, the band-like device at least partially follows the course of the myofascial line in the foot from the front edge of the lower leg outside the front edge of the shin in the direction of extension of the front shin muscle to the inside of the tarsus, from where the myofascial spiral line winds around the head of the anklebone (talus) and of the navicular bone and extends obliquely over the sole of the foot on the outside of the foot in the heelward direction of the base of the fifth metatarsal and then rises behind the lateral malleolus to the fibula and runs out at the head of the fibula.

According to a further embodiment, the band-like device is arranged on or integrated into the sole such that it crosses the shoe base starting from the location of the base of the fifth metatarsal of the foot arranged in the shoe.

According to one embodiment, the band-like device or one or more sections thereof extend at an angle of between 20° and 90°, in particular 30° and 80°, 40° and 70°, 50° and 60° or 60° and 70° (degrees) to the longitudinal direction of the sole.

According to one embodiment, the band-like device is integrated into the shoe sole or arranged on the top side or underside of the shoe sole. In particular, the band-like device can be firmly joined to the shoe sole or be produced in one piece with the shoe sole.

According to a further embodiment, the shoe sole has, on its top side or underside, a recess crossing the shoe sole, the band-like device being arranged in said recess.

According to a further embodiment, the band-like device can extend as an extension from one or from both sides of the sole. Preferably, the band-like device extends in the direction of one or more myofascial lines in the foot of the wearer, for example along the myofascial spiral line and at an angle to the longitudinal direction of the sole, as described above. The band-like device integrated into the sole can extend for example along a length of 1 cm, 2 cm, 3 cm, 4 cm, 5 cm, 6 cm, 7 cm, 8 cm, 9 cm, 10 em, 15 cm, 20 cm or more on one or on both sides of the sole. It is also possible for ends of a band-like device to extend from the sole on one side or both sides, said ends having a length which is selected such that they can be joined together over the foot or at least project out of the shaft of the shoe in order to be secured thereto.

According to one embodiment, those sections of the band-like device that proceed from the sole, with the sole arranged in a shoe, extend from the sole substantially vertically upwards in the direction of the shaft edge. However, it is also conceivable for one or both sections to extend upwards at an angle of between 0° and 45° with respect to the perpendicular to the sole of the shoe, in order to correspond better to the course of the myofascial lines in the foot. The angle can in particular be between 20° and 70°, between 30° and 60° or between 35° and 55°.

The band-like device integrated into or joined to the shoe sole can also have one or more properties, in particular in terms of design and configuration of the band-like device, which were described above in conjunction with the shoe which has a band-like device.

Also provided according to the invention is a sock which has a band-like device which extends from the upper end to the foot part of the sock on one inner side of the sock and from the foot part to the upper end on the opposite inner side of the sock, wherein the band-like device is designed to exert pressure on a foot arranged in the sock.

According to one embodiment, the band-like device is arranged in the sock such that it exerts pressure on at least one myofascial line of the foot. In particular, the band-like device can be arranged in or integrated into the sock such that it extends at least partially along one or more myofascial lines of the foot.

By way of the band-like device integrated into or joined to the sock, sections of the foot that are located in the region of the band-like device can be stimulated by exertion of pressure and thus the functions of the foot and of the lower leg that are impaired or disrupted in a conventional sock can be activated for the duration that the sock according to the invention is worn. The exerted pressure can be scarcely perceptible or clearly noticeable to the wearer of the sock depending on the configuration of the band-like device. It is also possible for the pressure exerted by the band-like device to vary in intensity in different regions of the band-like device. If the band-like device extends for example in the sock over the region of the Achilles tendon, the band-like device can be designed in a thinner manner or be hollowed at this point, in order to avoid rubbing on the foot.

According to a further embodiment, the band-like device has one or more sections which can be joined together or separate. One section of the band-like device can extend at an angle to the longitudinal direction of the foot region on the underside of the sock. According to another embodiment, the band-like device is arranged in the sock such that it crosses the foot part of the sock at the arch of the foot. According to yet another embodiment, the band-like device is arranged in the sock such that it crosses the foot part of the sock starting from the location of the base of the fifth metatarsal of the foot in the sock. The band-like device at least partially follows the course of the myofascial spiral line in the foot from the front edge of the lower leg outside the front edge of the shin in the direction of extension of the front shin muscle to the inside of the tarsus, from where the myofascial spiral line winds around the head of the anklebone (talus) and of the navicular bone and extends obliquely over the sole of the foot on the outside of the foot in the heelward direction of the base of the fifth metatarsal and then rises behind the lateral malleolus to the fibula and runs out at the head of the fibula.

According to one embodiment, the band-like device extends at an angle of between 20° and 90°, in particular 30° and 80°, 40° and 70°, 50° and 60° (degrees) to the longitudinal direction of the foot region of the sock on the underside of the latter.

The band-like device can be integrated into the sock. For example, the band-like device can be attached to the inner side or to the outer side of the sock or be arranged in a pocket integrated into the sock. The band-like device or sections thereof could also be woven into the material of the sock.

In the lateral regions of the sock, the band-like device extends substantially vertically upwards in the direction of the upper edge of the sock. The band-like device can extend as far as the upper edge of the sock. One or both sections of the sections of the band-like device that extend upwards on the sides of the sock can also extend at an angle of in particular between 20° and 70°, between 30° and 60° or between 35° and 55° with respect to the perpendicular to the underside or lower foot surface of the sock.

According to a further embodiment, the band-like device is arranged in or integrated into the sock such that it crosses the underside of the sock at the arch of the foot, in particular in the region of the talocalcaneonavicular joint. At this position, the band-like device is located opposite the myofascial spiral line on the underside of the foot. The sock can be produced from a textile material, from cotton, wool, synthetic material or a combination thereof.

The band-like device arranged in or integrated into the sock can also have one or more properties, in particular in terms of design and configuration of the band-like device, which were described above in conjunction with the shoe or the sole which have a band-like device.

BRIEF DESCRIPTION OF THE DRAWINGS

Further features, properties and advantages of the invention can be gathered from the following description of the invention on the basis of an exemplary embodiment and the appended drawing.

FIGS. 4A-4C show views of a sock according to one embodiment of the invention from below (FIG. 4A), in a view from the outside (FIG. 4k), and in a view from the inside (FIG. 4C) according to one embodiment of the invention FIG. 5 shows the course of the myofascial spiral line in the human foot seen in FIG. 2A and further includes the angles between which the myofascial spiral line can cross the human foot. Also shown is the angle of the myofascial spiral line in FIG. 2A.

DETAILED DESCRIPTION

Figures 2A, 2B, 2C:
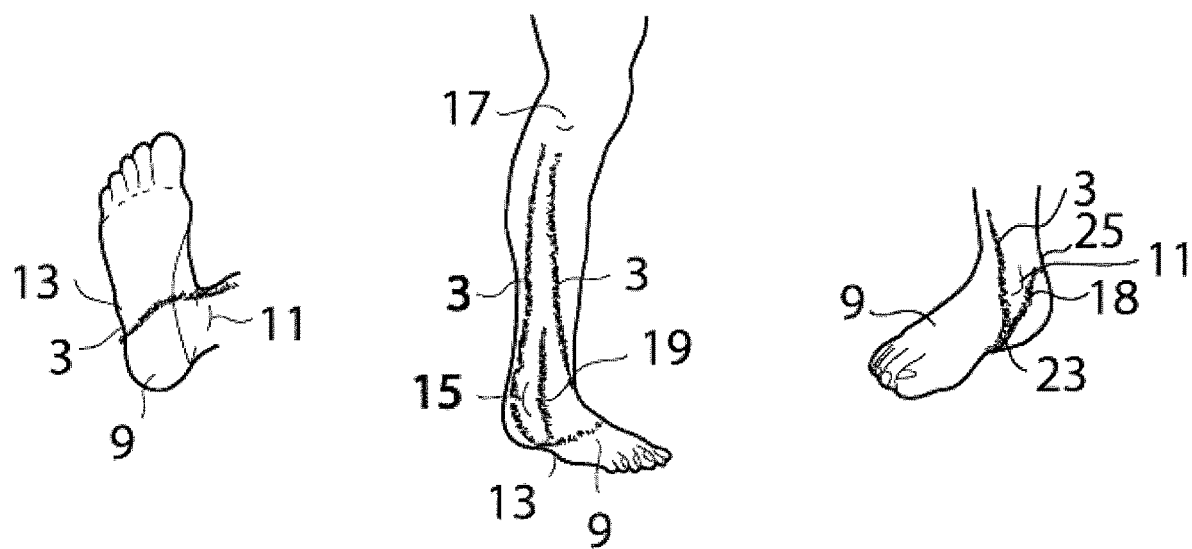
FIGS. 2A-2C show the course of the myofascial spiral line in the human foot in a view from below (FIG. 2A), in a view from the outside (FIG. 2B), and in a view from the inside (FIG. 2C) corresponding to the course of the band-like device in a shoe.
Figure 3A:
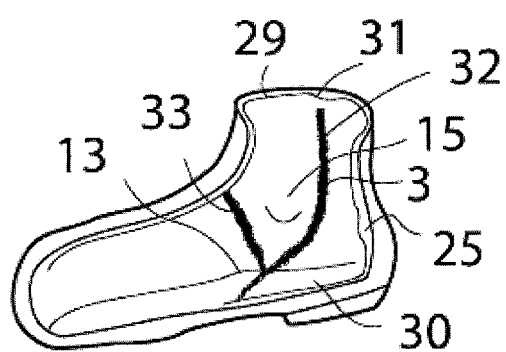
FIGS. 3A-3B show views of the inner side of a shoe on the outside of the shoe (FIG. 3A) and inside of the shoe (FIG. 3B), respectively.
Figure 3B:
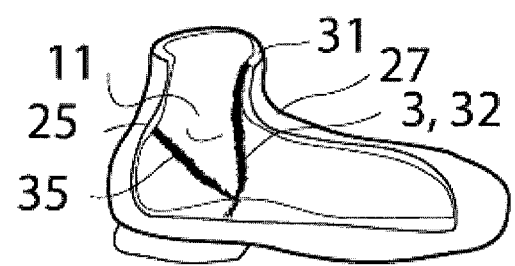

An embodiment of the invention is described in the following text with reference to the figures. FIG. 2A shows a foot obliquely from below, wherein the medial malleolus 11 is indicated. In a shoe 27, as shown in FIGS. 3A and 3B, the course of the band-like device at least partially follows the myofascial spiral line 3, which extends from the front side of the shin edge around the head of the talus and the navicular bone under the arch 23 of the foot to the outside of the foot 9 behind the base 13 of the fifth metatarsal.

FIG. 2B illustrates the foot 9 from outside. The myofascial spiral line 3 appears, coming from the sole of the foot, on the outside of the foot behind the base 13 of the fifth metatarsal and extends in the direction of the Achilles tendon 25 and behind the lateral malleolus 15 in the direction of the head 17 of the fibula and in the process approaches the internally extending line of the myofascial spiral line 3. The band-like device 32 in the shoe 27 at least partially follows the course of the myofascial spiral line 3. The band-like device 32 can extend at an angle to the longitudinal direction of the sole of between 20° and 90°, as shown in FIG. 5. In particular embodiments, the band-like device can extend at an angle to the longitudinal direction of the sole that is between 30° and 80°, between 40° and 70°, between 50° and 60°, or between 60° and 70°.

According to one embodiment, an extension 33 of the band-like device 32 is provided on the outside of the shoe 27, said extension 33 starting at the point at which the band-like device, following the myofascial spiral line 3, appears, coming from the sole of the foot, behind the base of the fifth metatarsal 13 on the outside of the foot. The extension 33 of the band-like device can be joined to the band-like device 32 or be separate therefrom. It extends, following the myofascial line 19, upwards in front of the lateral malleolus 15 to the lower leg and approximately parallel to the course of the line of the band-like device 32 following the myofascial spiral line 3.

FIG. 2C illustrates the foot 9 in the view from the inside. The myofascial spiral line 3 extends, coming from the front shin edge, in front of the medial malleolus 11 at the point at which the arch 23 of the foot is distinct, and under the sole of the foot. Located thereabove are the navicular bone and the head of the talus. The band-like device 32 in the shoe 27 at least partially follows the course of the myofascial spiral line 3 on this side of the foot.

According to a further embodiment, the band-like device 32 can be extended by a further band-like device 35 on the inside of the shoe following a myofascial line 18. This additional band-like device 35 starts, following the myofascial spiral line 3, in the region of the arch 23 of the foot or navicular bone at the band-like device 32 and extends upwards on the inside of the heel. According to one embodiment, it can be continued or lengthened and, above the heel bone, cross the region of the Achilles tendon 25 and, on the opposite outside of the foot, meet the outer line of the band-like device 32 following the myofascial spiral line 3 extending there (this extension is not illustrated in FIG. 3A). In the region of the crossing of the Achilles tendon 25, the thickness and/or the hardness of the band-like device 35 can change, in particular be reduced or hollowed, in order to avoid rubbing effects on the Achilles tendon 25.

In FIGS. 3A and 3B, the invention is demonstrated on a cutaway shoe according to one embodiment. In FIG. 3A, the shoe 27 is illustrated in a cutaway manner, wherein the little-toe side in the shoe 27, corresponding to the position of the outside of the shoe 27, can be seen. The inner lining 29 of the shoe is likewise illustrated in a cutaway manner. At a thickened portion 31 of the inner lining at the upper shaft edge, the course of the prominent band-like device 32 according to the invention can be seen. This extends, following the myofascial spiral line 3, behind the indicated lateral malleolus 15 of the foot in the shoe 27, first of all substantially vertically downwards. The band-like device 32 crosses the shoe base 30 or passes under the sole of the foot starting on the little-toe side of the shoe 27, or outside of the foot, approximately behind the position of the base 13 of the indicated fifth metatarsal of the foot in the shoe. An additional band-like device 33, following the myofascial line 19 shown in FIG. 2B, can extend from the original band-like device 32 on the little-toe side of the inside of the shoe 27 in front of the position of the lateral malleolus 15 in the shoe in the region of the instep.

The cutaway illustration of the shoe 27 in FIG. 3B shows a view of the big-toe side of the inside of the shoe. The band-like device 32 according to the invention extends, following the myofascial spiral line 3, in front of the position of the medial malleolus 11 in the shoe 27 substantially vertically from the shaft edge and crosses the shoe base or passes under the sole of the foot in the region of the head of the talus and the navicular bone approximately at the point at which the longitudinal arch 23 of the foot 9 is located. At the thickened portion 31 at the upper edge of the shaft it is apparent that the band-like device 32 extends into the shoe 27 from above, laterally to the edge of the shin. The band-like device 32 can be extended on the big-toe side of the shoe 27 by an additional band-like device 35, which extends at the turnup of the band-like device 32, starting from the band-like device 32 at the position of the arch of the foot in the shoe, in the heelward direction towards the position of the Achilles tendon 25 above the heel bone. The additional band-like device 35 can be thinned or hollowed in the region of the Achilles tendon 25 and its course can continue in the inner lining 29 on the outside of the shoe 27. The additional band-like devices 33, 35 can be formed from the same material as the corresponding sections of the band-like device 3 from which they proceed, or from a different material. For example, the additional band-like devices 33, 35 can be formed by cushioning, while the band-like device 3 is formed from a cord material, or vice versa.

FIGS. 4A to 4C show a sock 37 according to one embodiment of the invention in various views. FIG. 4A shows the sock 37 obliquely from below. The course of the band-like device 39 at least partially follows, on the sock 37, the myofascial spiral line 3, which extends from the front side of the shin edge around the head of the talus and the navicular bone under the arch 23 of the foot to the outside of the foot 9 behind the base 13 of the fifth metatarsal, as specified above in conjunction with the shoe 27.

Figure 1:
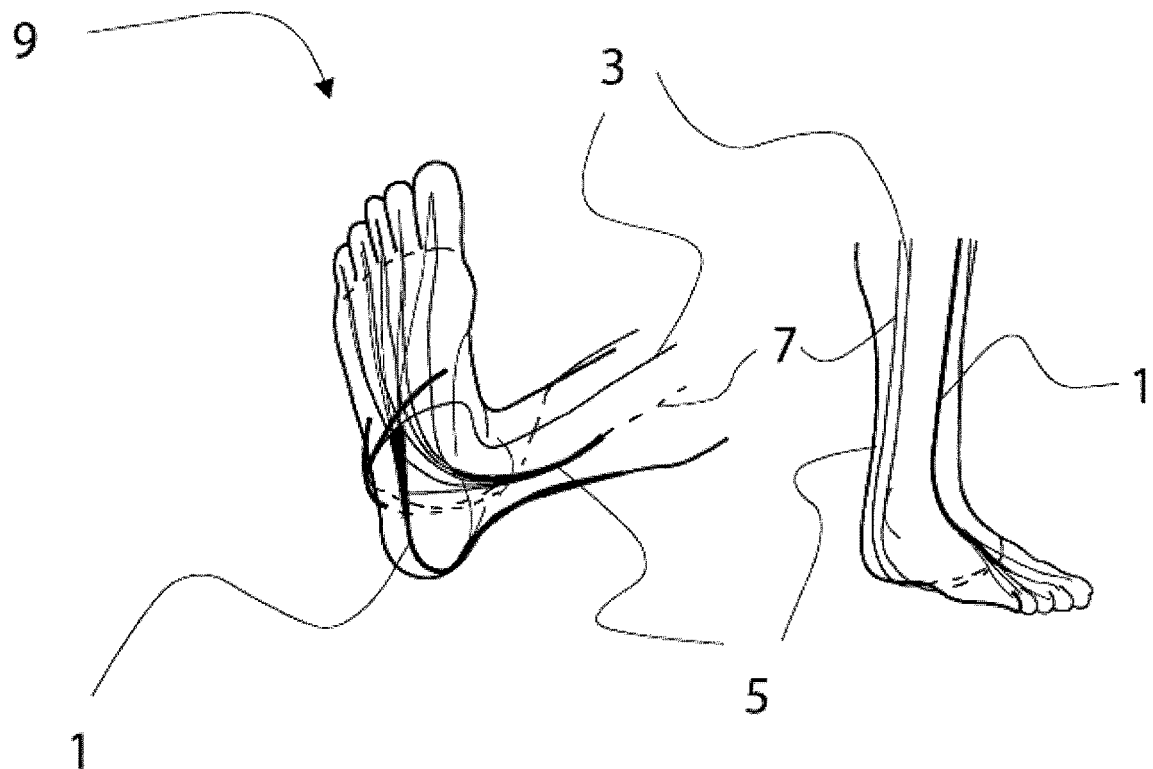
FIG. 1 shows the course of the myofascial lines in the human foot.

FIG. 4B illustrates the sock 37 from the outside. As described above, the myofascial spiral line 3 appears, coming from the sole of the foot, on the outside of the foot behind the base 13 of the fifth metatarsal and extends in the direction of the Achilles tendon and behind the lateral malleolus 15 in the direction of the head 17 of the fibula (see FIG. 1). The band-like device 39 in the sock 37 at least partially follows the course of the myofascial spiral line 3, at least as far as the cuff 41 of the sock 37.

According to one embodiment, as in the shoe, an extension 40 of the band-like device 39 is provided on the outside of the sock 37, which starts at the point at which the band-like device 39, following the myofascial spiral line 3, appears, coming from the sole of the foot, behind the base of the fifth metatarsal 13 on the outside of the foot. The extension 40 of the band-like device can be joined to the band-like device 39 or be separate therefrom. It extends, following the myofascial line 19, upwards in front of the lateral malleolus 15 to the lower leg and approximately parallel to the course of the line of the band-like device 39 following the myofascial spiral line 3 (see FIG. 2B).

FIG. 4C illustrates the sock 37 in the view from the inside. As already described above and shown in FIG. 2C, the myofascial spiral line 3 extends, coming from the front shin edge, in front of the medial malleolus 11 at the point at which the arch 23 of the foot is distinct, and under the sole of the foot. Located thereabove are the navicular bone and the head of the talus. The band-like device 39 in the sock 37 at least partially follows the course of the myofascial spiral line 3 on this side of the foot 9.

According to a further embodiment, the band-like device 39 can be extended by a further band-like device (not shown) on the inside of the sock 37 following the myofascial line 18. This additional band-like device starts, following the myofascial spiral line 3, in the region of the arch 23 of the foot or navicular bone at the band-like device 39 and extends upwards on the inside of the heel, crosses, above the heel bone, the region of the Achilles tendon 25 and meets, on the opposite outside of the foot, the outer line of the band-like device 39 following the myofascial spiral line 3 extending there. In the region of the crossing of the Achilles tendon 25, the thickness and/or the hardness of the band-like device 39 in the sock can change, in particular be reduced or hollowed, in order to avoid rubbing effects on the Achilles tendon 25.

Numerous modifications can be made to the described invention and the illustrated embodiments, without departing from the scope of the invention.

EMBODIMENTS

Embodiment 1. The shoe which has a band-like device (32) which extends from the upper shaft end to the shoe base on one inner side of the shoe (27) and extends from the shoe base in the direction of the upper shaft end on the opposite inner side of the shoe (27), wherein the band-like device (32) is designed to exert pressure on a foot (9) arranged in the shoe (27).

Embodiment 2. The shoe according to Embodiment 1, wherein the band-like device (32) is arranged in the shoe (27) such that it exerts pressure on at least one myofascial line (1, 3, 5, 7) of the foot (9).

Embodiment 3. The shoe according to either of Embodiments 1 and 2, wherein the band-like device (32) is arranged in the shoe (27) such that it crosses the shoe base starting from the location of the base (13) of the fifth metatarsal of the foot (9) in the shoe (27).

Embodiment 4. The shoe according to one of Embodiments 1 to 3, wherein the band-like device (32) is arranged at least partially under the inner lining (29) of the shoe (27) or is configured as part of the inner lining (29) of the shoe (27).

Embodiment 5. The shoe according to one of Embodiments 1 to 4, wherein the band-like device (32) is configured as a cushion or as a flat band made of a fabric or textile.

Embodiment 6. Shoe according to one of Embodiments 1 to 5, wherein the band-like device (32) is formed at least sectionally from an elastic material.

Embodiment 7. The shoe according to one of Embodiments 1 to 6, wherein the shoe (27) has, on the outer side of the shaft, at least one opening, through which one end of the band-like device (32) can be passed from the inside of the shoe (27) to the outside.

Embodiment 8. The shoe according to one of Embodiments 1 to 7, wherein at least one channel or one or more eyelets or loops are formed in the inner lining (29) or on the inner side of the shoe (27) under the inner lining (29), the band-like device (32) being able to be received therein.

Embodiment 9. The shoe according to one of Embodiments 1 to 8, wherein the band-like device (32) has two ends, at least one of which branches into two ends.

Embodiment 10. The shoe according to one of Embodiments 1 to 9, wherein the band-like device (32) has a fastener, with which the two ends of the band-like device (32) can be joined together.

Embodiment 11. The shoe according to one of Embodiments 1 to 10, wherein at least one end of the band-like device (32) is joined to the lacing or at least one end of the band-like device (32) is secured to the shoe (27).

Embodiment 12. The shoe sole which has a band-like device (32) which is joined to the sole and extends at an angle to the longitudinal direction of the sole, wherein the band-like device (32) is designed, when it is arranged in a shoe (27), to exert pressure on a foot (9) arranged in the shoe (27).

Embodiment 13. The shoe sole according to Embodiment 12, wherein the band-like device (32) or one or more sections thereof extend(s) at an angle of between 20° and 90°, in particular 30° and 80°, 40° and 70°, 50° and 60° or 60° and 70° to the longitudinal direction of the sole.

Embodiment 14. The shoe sole according to Embodiments 12 or 13, wherein the band-like device (32) extends along one or more myofascial lines on the foot (9) of the wearer.

Embodiment 15. The sock which has a band-like device (39) which extends from the upper end to the foot part of the sock (37) on one inner side of the sock (37) and from the foot part to the upper end on the opposite inner side of the sock (37), wherein the band-like device (39) is designed to exert pressure on a foot (9) arranged in the sock (37).

Embodiment 16. Sock according to Embodiment 15, wherein the band-like device (39) is arranged in the sock (37) such that it exerts pressure on at least one myofascial line (1, 3, 5, 7) of the foot (9).

Embodiment 17. The sock according to Embodiment 15 or 16, wherein the band-like device (39) is arranged in the sock (37) such that it crosses the foot part of the sock (37) at the arch of the foot.

Embodiment 18. The sock according to one of Embodiments 15 to 17, wherein the band-like device (39) is arranged in the sock (37) such that it crosses the foot part starting from the location of the base (13) of the fifth metatarsal of the foot (9) in the sock (37).

REFERENCE SIGNS 1, 5, 7 Myofascial lines
3 Myofascial spiral line
9 Foot
11 Medial malleolus
13 Base of the fifth metatarsal
15 Lateral malleolus
17 Head of the fibula
19 Myofascial line
21 Navicular bone
23 Arch of the foot
25 Region of the Achilles tendon
27 Shoe
29 Inner lining
30 Shoe base
31 Thickened portion
32 Band-like device
33 Additional band-like device
35 Additional band-like device
37 Sock 39 Band-like device on the sock
40 Extension of the band-like device on the sock
41 Sock cuff

The invention claimed is:

1. A shoe, configured to be worn on a foot of a user, the shoe comprising:
a shoe base;
a shaft, wherein the shaft comprises:
an upper shaft end; and
a band, configured to follow at least one myofascial line in a foot of a user arranged in the shoe, wherein the myofascial line extends downward from a lower leg and forward of a medial malleolus and crosses a sole of the foot at a heelward angle to a longitudinal arch of the foot, so as to extend upward and toward the lower leg behind a lateral malleolus,
wherein the band is fixed to an interior side of the shaft at a medial side of the shoe so that the band extends entirely on the interior side of the shoe in a direction from the upper shaft end to the shoe base and traverses the shoe base across the longitudinal arch direction of the shoe base in a heelward direction towards a position at a lateral side of the shoe and wherein the band further extends upwards in a direction of the upper shaft end at a position configured to be located behind the lateral malleolus, wherein the band is configured to contact the foot of the user arranged in the shoe and configured to exert pressure on the at least one myofascial line of the foot of the user arranged in the shoe.

2. The shoe according to claim 1,
wherein the band is arranged in the shoe such that, when the foot of the user is arranged in the shoe, the band crosses the shoe base at a location configured to start from the base of the fifth metatarsal of the foot arranged in the shoe.

3. The shoe according to claim 1,
wherein the band is arranged at least partially under an inner lining of the shoe or is configured as part of the inner lining of the shoe.

4. The shoe according to claim 1,
wherein the band is configured as a cushion or as a flat band made of a fabric or textile.

5. The shoe according to claim 1,
wherein the band is formed at least sectionally from an elastic material.

6. The shoe according to claim 1,
wherein the band has two ends, and
wherein at least one end of the two ends branches into two branched ends.

7. The shoe according to claim 6,
wherein at least one branched end of the two branched ends of the band ends at the shoe base and is secured to the interior side of the shoe base there.

8. The shoe according to claim 1, wherein the band has a width and a position in the shoe so that the band is configured to symmetrically overlap the at least one myofascial line on both sides of the shoe and perpendicular to the longitudinal direction of the sole of the foot of the user.

9. A sole assembly, configured to be arranged in a shoe, the sole assembly comprising:
an inner sole; and
a band, configured to follow at least one myofascial line in a foot of a user arranged in the shoe, wherein the at least one myofascial line extends downward from a lower leg and forward of a medial malleolus,
wherein the band forms part of the inner sole or is integrated therein so that the band extends medially at an angle of less than 70 degrees to a longitudinal direction of the inner sole,
wherein, when the sole assembly is arranged in the shoe, the band extends entirely on an interior side of a shaft of the shoe at a medial side of the shoe in a direction from an upper shaft end of the shoe to a shoe base of the shoe and is connected to the inner sole, the connection being configured in a region of a talocalcaneonavicular joint of the foot,
wherein, when the sole assembly is arranged in the shoe, the band is configured to be arranged between the interior side of the shoe and the foot of the user and is configured to contact the foot of the user arranged in the shoe to exert pressure on the at least one myofascial line of the foot of the user arranged in the shoe.

10. The sole assembly according to claim 9,
wherein the band, or at least one section thereof, extends at an angle of between 20° and 69° to the longitudinal direction of the inner sole.

11. The sole assembly according to claim 10,
wherein the angle is between 60° and 69°.

* * * * *